(12) United States Patent
Ballard et al.

(10) Patent No.: US 10,492,917 B2
(45) Date of Patent: *Dec. 3, 2019

(54) INTRABODY OSTEOTOMY IMPLANT AND METHODS OF USE

(71) Applicant: Warsaw Orthopedic, Inc., Warsaw, IN (US)

(72) Inventors: Rodney Ray Ballard, Lakeland, TN (US); David A. Mire, Cordova, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 42 days.

This patent is subject to a terminal disclaimer.

(21) Appl. No.: 15/727,086

(22) Filed: Oct. 6, 2017

(65) Prior Publication Data
US 2018/0028327 A1    Feb. 1, 2018

Related U.S. Application Data

(60) Continuation-in-part of application No. 15/262,680, filed on Sep. 12, 2016, now abandoned, which is a
(Continued)

(51) Int. Cl.
*A61F 2/44* (2006.01)
*A61B 17/70* (2006.01)
(Continued)

(52) U.S. Cl.
CPC ............ *A61F 2/44* (2013.01); *A61B 17/7001* (2013.01); *A61B 17/708* (2013.01);
(Continued)

(58) Field of Classification Search
CPC ............ A61B 17/7001; A61B 17/7032; A61B 17/7077; A61B 17/8095; A61B 2017/681;
(Continued)

(56) References Cited

U.S. PATENT DOCUMENTS 6,159,211 A * 12/2000 Boriani ................ A61F 2/44
606/247
6,241,771 B1    6/2001 Gresser et al.
(Continued)

OTHER PUBLICATIONS

European Search Report for EP 14848940.4 date of completion is dated Apr. 25, 2017 (2 pages).
(Continued)

*Primary Examiner* — Lynnsy M Summitt

(57) ABSTRACT

Methods for surgically adjusting a curvature of a spine are disclosed. The methods provide for controlling the alignment of bony structures, such as vertebral bodies or portions thereof, as they are moved relative to one another during a surgical procedure. An intrabody implant disclosed and methods of use are also disclosed. The implant has an inclined surface, forming a wedge or other shape having, for example, an acute angle adapted to be placed between at least two separated portions of a single bony structure (such as a vertebral body). In some embodiments, the implant may be used to support portions of a vertebral body that have been separated surgically as part of a pedicle subtraction osteotomy and to orient the portions at a more predictable lordotic angle.

18 Claims, 13 Drawing Sheets

US 10,492,917 B2
Page 2

Related U.S. Application Data division of application No. 14/037,737, filed on Sep. 26, 2013, now Pat. No. 9,456,856.

(51) Int. Cl.
*A61B 17/80* (2006.01)
*A61F 2/30* (2006.01)

(52) U.S. Cl.
CPC ...... *A61B 17/7032* (2013.01); *A61B 17/7083* (2013.01); *A61B 17/7085* (2013.01); *A61B 17/8095* (2013.01); *A61F 2/30* (2013.01); *A61F 2/30767* (2013.01); *A61F 2002/3093* (2013.01); *A61F 2002/4475* (2013.01); *A61F 2210/0014* (2013.01); *A61F 2220/0016* (2013.01); *A61F 2230/0015* (2013.01); *A61F 2310/00017* (2013.01); *A61F 2310/00023* (2013.01); *A61F 2310/00029* (2013.01); *A61F 2310/00293* (2013.01); *A61F 2310/00329* (2013.01); *A61F 2310/00359* (2013.01); *A61F 2310/00371* (2013.01)

(58) Field of Classification Search
CPC ..... A61B 17/708; A61B 17/885; A61B 17/56; A61F 2/4455; A61F 2002/4475; A61F 2/4611; A61F 2310/00023; A61F 2002/3093; A61F 2002/2835; A61F 2002/30281
See application file for complete search history.

(56) References Cited

U.S. PATENT DOCUMENTS

| | | | |
|---|---|---|---|
| 6,287,308 B1 * | 9/2001 | Betz | A61B 17/7044 606/246 |
| 6,648,885 B1 * | 11/2003 | Friesem | A61B 17/7002 606/250 |
| 6,648,891 B2 * | 11/2003 | Kim | A61B 17/0206 606/102 |
| 7,118,579 B2 | 10/2006 | Michelson | |
| 7,238,203 B2 | 7/2007 | Bagga et al. | |
| 7,238,206 B2 * | 7/2007 | Lange | A61F 2/4465 623/17.11 |
| 7,655,027 B2 | 2/2010 | Michelson | |
| 7,686,814 B2 | 3/2010 | Lim et al. | |
| 7,922,729 B2 | 4/2011 | Michelson | |
| 8,092,464 B2 | 1/2012 | McKay | |
| 8,147,521 B1 * | 4/2012 | Cornwall | A61B 17/7001 606/265 |
| 8,439,977 B2 | 5/2013 | Kostuik et al. | |
| 8,663,289 B2 | 3/2014 | Schwab | |
| 8,727,972 B2 | 5/2014 | Zhang et al. | |
| 8,771,321 B2 | 7/2014 | Michelson | |
| 8,828,059 B2 | 9/2014 | Steele | |
| 9,402,660 B2 | 8/2016 | Brinkman et al. | |
| 9,795,418 B2 * | 10/2017 | Perry | A61B 17/7044 |
| 2002/0087212 A1 | 7/2002 | James et al. | |
| 2005/0010292 A1 * | 1/2005 | Carrasco | A61F 2/4455 623/17.11 |
| 2006/0100705 A1 | 5/2006 | Puno et al. | |
| 2009/0062917 A1 | 3/2009 | Foley et al. | |
| 2011/0015745 A1 | 1/2011 | Bucci | |
| 2013/0123786 A1 * | 5/2013 | McCormack | A61B 17/1671 606/82 |
| 2017/0105844 A1 | 4/2017 | Kuyler et al. | |
| 2017/0209182 A1 | 7/2017 | Picetti et al. | |
| 2017/0216045 A1 | 8/2017 | Dewey et al. | |
| 2017/0216051 A1 | 8/2017 | Dewey | |

OTHER PUBLICATIONS

International Search Report for PCT/US2014/054556 date of completion is dated Dec. 16, 2014 (2 pages).

* cited by examiner

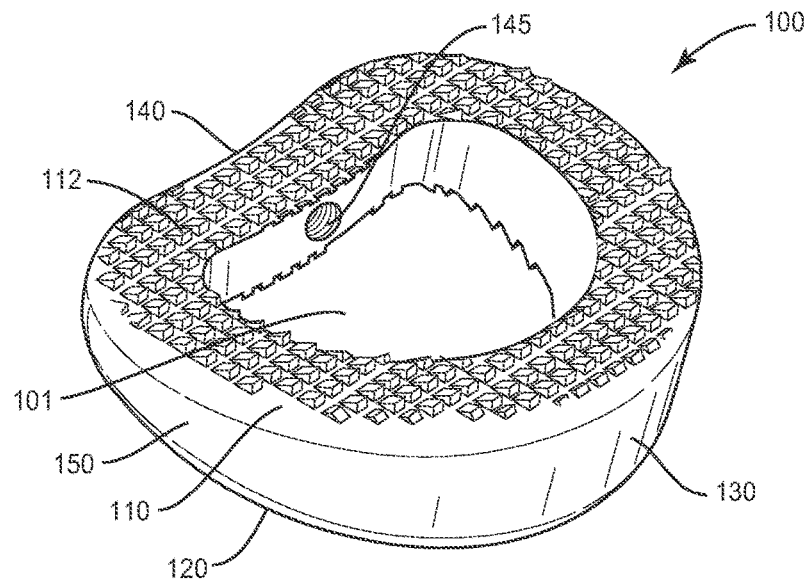
FIG. 4
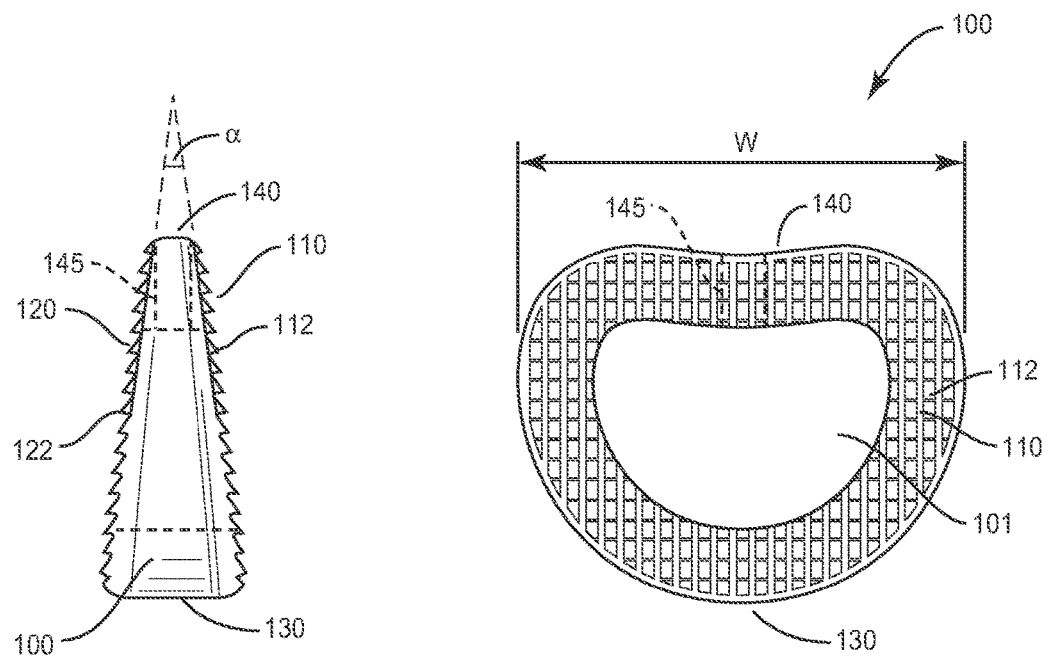
FIG. 5
FIG. 6

INTRABODY OSTEOTOMY IMPLANT AND METHODS OF USE

CROSS-REFERENCE TO RELATED APPLICATIONS

The present application is a Continuation-in-Part of U.S. patent application Ser. No. 15/262,680, filed on Sep. 12, 2016, which is a Divisional of U.S. patent application Ser. No. 14/037,737, filed on Sep. 26, 2013, issued as U.S. Pat. No. 9,456,856, which are incorporated herein by reference in their entirety.

TECHNICAL FIELD

The present disclosure generally relates to medical devices, systems and methods for the treatment of musculoskeletal disorders, and more particularly, to an intrabody implant and methods for fusing portions of one or more vertebral bodies to achieve a desired spinal curvature and/or angulation.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility. For example, after a disc collapse, severe pain and discomfort can occur due to the pressure exerted on nerves and the spinal column.

Non-surgical treatments, such as medication, rehabilitation and exercise can be effective, however, may fail to relieve the symptoms associated with these disorders. Surgical treatment of these spinal disorders includes fusion, fixation, discectomy, laminectomy, osteotomy and implantable prosthetics. These treatments may employ spinal implants and, in some cases, the placement of interbody implants via a variety of invasive, partially invasive and/or minimally invasive surgical pathways. Furthermore, in spinal disorders wherein a patient has an abnormal spinal curvature, surgeons may perform a complete and/or partial osteotomy to remove bony structures from the spine in order to reorient the bones of the spine to provide the patient with a desired spinal curvature. In many cases, however, there is difficulty in providing an accurate kyphotic and/or lordotic angle when performing osteotomy. Various factors contribute to this difficulty, including, but not limited to: the challenge of cutting a wedge-shaped aperture in the spinal anatomy having a precise slope; and the breakdown or subsidence of the remaining bony portions after an osteotomy is performed. This disclosure describes an improvement in these technologies.

SUMMARY

Accordingly, methods for surgically adjusting a curvature of a spine comprising vertebrae are disclosed. Such methods may include steps of removing a portion of a single vertebral body of the spine to form two at least partially separated portions of the vertebral body; inserting a first pedicle screw into a second vertebral body superior to the single vertebral body and a second pedicle screw into a third vertebral body inferior to the single vertebral body, connecting the first pedicle screw and the second pedicle screw with a rod; and bringing into closer proximity the two at least partially separated portions of the single vertebral body such that the first and second pedicle screw advance towards one another along the rod. The method embodiments may result in the orientation of the two at least partially separated portions of the vertebral body at a correction angle relative to one another.

The method embodiments described herein may provide lordotic and/or kyphotic correction to a spinal column at the level of the single vertebral body or across multiple levels, as part of an osteotomy procedure that may include, but is not limited to, a pedicle subtraction osteotomy (PSO). The step of bringing into closer proximity disclosed herein may include bringing the exposed portions of the screws and/or screw heads in closer proximity and/or angulating portions of the vertebrae or vertebral portions such that at least the posterior portions of the vertebrae or vertebral portions are brought closer together and further may include securing the two at least partially separated portions of the single vertebral body relative to one another using an extradiscal stabilization system. The method may further comprise repeating any or all of the removing, inserting, connecting steps, and the bringing into closer proximity the two at least partially separated portions of the single vertebral body (or alternatively two different vertebral bodies) step, across one, two, or more levels of the human spine to achieve an overall spinal correction across the one or more levels.

Furthermore, the method may also comprise providing a wedge-shaped intrabody implant comprising a first surface and a second surface, the second surface disposed at an acute angle to the first surface; and placing the wedge-shaped intrabody implant between the two at least partially separated portions of the single vertebral body. The method may also further comprise packing the intrabody implant with bone-growth promotion material (in a bone growth aperture defined in the intrabody implant, for example). In some embodiments, the acute angle is between 10 degrees and 30 degrees, or between 15 degrees and 25 degrees.

In some embodiments, the first pedicle screw is positioned on a lateral side of spinous processes of the second vertebral body, and wherein the second pedicle screw is positioned on the same lateral side of spinous processes of the third vertebral body. The method may further comprise inserting a third pedicle screw into the second vertebral body on a lateral side of spinous processes opposite the first pedicle screw and a fourth pedicle screw into the third vertebral body on a lateral side of spinous processes opposite the second pedicle screw, and connecting the third pedicle screw and the fourth pedicle screw with a second rod. During the step of bringing into closer proximity the two at least partially separated portions of the single vertebral body (or alternatively two different vertebral bodies), the third and fourth pedicle screw may advance towards one another along the second rod.

In some embodiments, the first and second pedicle screws are dual headed screws and the rod connects a first head of the first pedicle screw with a first head of the second pedicle screw. The method may further comprise inserting a third pedicle screw in a vertebrae superior to the first pedicle screw and a fourth pedicle screw in a vertebrae inferior to the second pedicle screw, wherein the step of bringing into closer proximity further comprises securing the two at least partially separated portions of the single vertebral body (or multiple different vertebral bodies) relative to one another by connecting the first, second, third, and fourth pedicle screws with a second rod. The second rod connects a second head of the first pedicle screw with a second head of the second pedicle screw. Alternatively, offset connectors may be applied or inserted into one or more screw heads to effectively create multi-headed screws in place of or in addition to the use of one or more dual-headed screws.

Also provided is a method for surgically adjusting a curvature of a spine comprising vertebrae, the method comprising removing a portion of at least one vertebral body to form an opening in the spine, inserting a first pedicle screw into a vertebral body or portion thereof superior to the opening and a second pedicle screw into a vertebral body or portion thereof inferior to the opening, connecting the first pedicle screw and the second pedicle screw with a rod, and bringing into closer proximity the superior vertebral body or portion thereof and inferior vertebral body or portion thereof such that the first and second pedicle screw advance towards one another along the rod. In some embodiments, the first and second pedicle screws are dual headed screws and the rod connects a first head of the first pedicle screw with a first head of the second pedicle screw. The method may further comprising inserting a third pedicle screw in a vertebrae superior to the first pedicle screw and a fourth pedicle screw in a vertebrae inferior to the second pedicle screw, wherein the step of bringing to closer proximity further comprises securing the inferior vertebral body or portion thereof to the inferior vertebral body or portion thereof by connecting the first, second, third, and fourth pedicle screws with a second rod. In some embodiments, removing a portion of at least one vertebral body further comprises removing at least one half of said vertebral body, and further comprises removing a portion of a vertebral disc associated with said vertebral body. In some embodiments, the first pedicle screw is inserted into a vertebral body that is a first vertebral body and the second pedicle screw is inserted into a vertebral body that is a second vertebral body such that the bringing into closer proximity brings a first vertebral body into closer proximity with a second vertebral body.

Also disclosed are an intrabody implant and methods of use. In one embodiment, an intrabody implant is provided for placement between separated portions of a previously-unitary bony structure, such as a vertebral body. In one embodiment, the intrabody implant comprises first and second surfaces for engaging the first and second portions of the separated bony structure. The surfaces of the implant may be provided with titanium or other coatings or a plurality of surface features extending outward from the surfaces to engage the bony structure. The second implant surface may be disposed opposite the first implant surface at an acute angle relative to the first surface. The implant further comprises a wall disposed between the first and second implant surfaces. The wall comprises anterior and posterior portions wherein the respective heights of the posterior and anterior portions are unequal to form the acute angle. In some embodiments, the implant may be made of any biocompatible material, such as metal, bone, plastic, coral, or other artificial or natural substances, and may additionally have naturally occurring or manufactured porous or roughened surfaces, or other surface features (for example, teeth or ridges) to facilitate engagement of the implant with portions of the spine. In some embodiments, the implant may further include openings for use with insertion instruments or fixation elements such as screws, nails or pins or for the further attachment of one or more plates or tabs.

Various embodiments of the intrabody implant may define an aperture extending through the implant to allow for bone growth through the implant. Furthermore, in some embodiments, the posterior height of the implant may be less than the anterior height of the implant such that the acute angle (which may range widely from 0-90 degrees) introduces a lordotic angle between the first and second portions of the bony structure when the intrabody implant is placed therebetween. The intrabody implant portions may also be formed of a polymer material such as PEEK, and be formed with a convex posterior portion and a concave anterior portion to better conform to the anatomy of the separated bony structure. The implant may also be sized to occupy a substantial width of the bony structure. For example, a width of the implant may, in some embodiments, be greater than 40 mm.

BRIEF DESCRIPTION OF THE DRAWINGS

The present disclosure will become more readily apparent from the specific description accompanied by the following drawings, in which:

FIG. 4 is a perspective view of an intrabody implant, according to one embodiment.

FIG. 5 is a side view of an intrabody implant, according to one embodiment.

FIG. 6 is a top view of an intrabody implant, according to one embodiment.

DETAILED DESCRIPTION

The exemplary embodiments of an intrabody implant and related methods of use disclosed herein are discussed in terms of medical devices for the treatment of musculoskeletal disorders and more particularly, in terms of an intrabody implant for placement after osteotomy and related methods for treating a vertebral column. It is envisioned that the disclosed intrabody implant and methods may provide, for example, a means for more accurately introducing a correction angle to a portion of the spinal column by virtue of the intrabody implant, which may enable a surgeon to more precisely predict the closure and/or correction angle despite variations in wedge angle that may be introduced in the "bone-on-bone" closure of known osteotomy procedures. In one embodiment, the wedge design of the intrabody implant may aid in the maintenance of anterior vertebral body height while allowing for closure (height collapse) on a posterior portion of the same vertebral body in order to introduce a corrective angulation.

The various embodiments described herein may also be especially useful in maintaining the shape and position of the vertebral body during and after an osteotomy. For example, in known osteotomy procedures as a wedge-cut vertebral body (see FIG. 2, for example) collapses, the anterior portion of the vertebral body (V1, V2) may also break during closure of the angle θ. It may be difficult for a surgeon to predict any shifts that may occur once the anterior portion of the vertebral body breaks. Thus, the intrabody implant 100 (see FIG. 3, for example) may help restrict any shift in the bony structures V1, V2 remaining after an osteotomy procedure. Further, a guided closure method (see FIGS. 8-16, for example) may also help restrict or further limit any shift in the bony structures V1 and V2 remaining after an osteotomy procedure.

Figure 1:
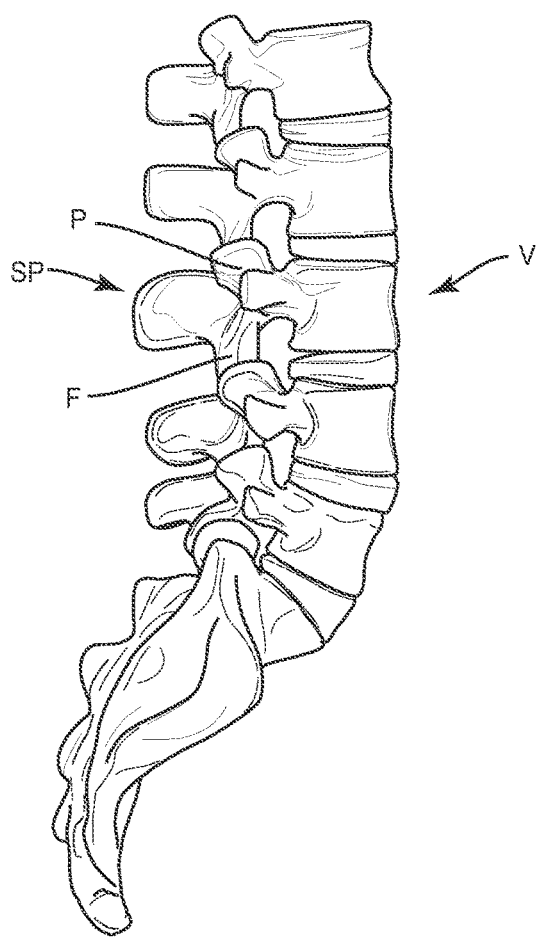
FIG. 1 is a perspective view of a spine with insufficient lordosis in the lumbar region.
Figure 2:
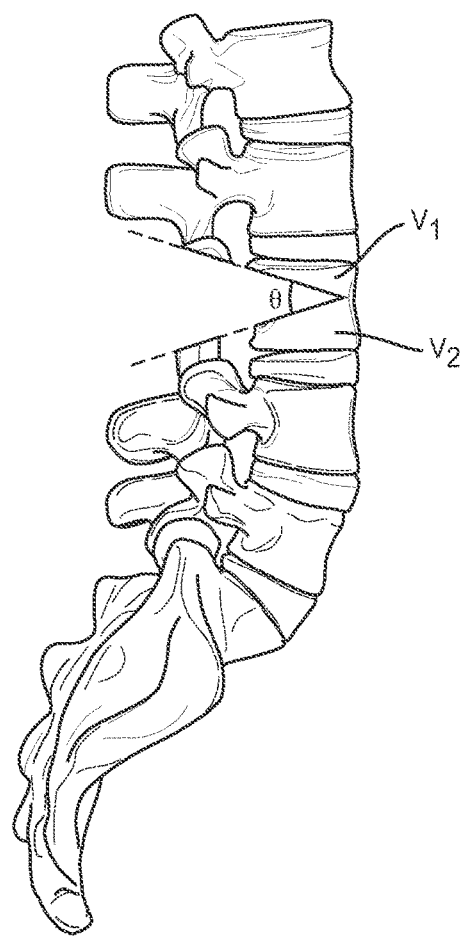
FIG. 2 is a perspective view of a spine after the initial removal of bony material from an osteotomy procedure.
Figure 3:
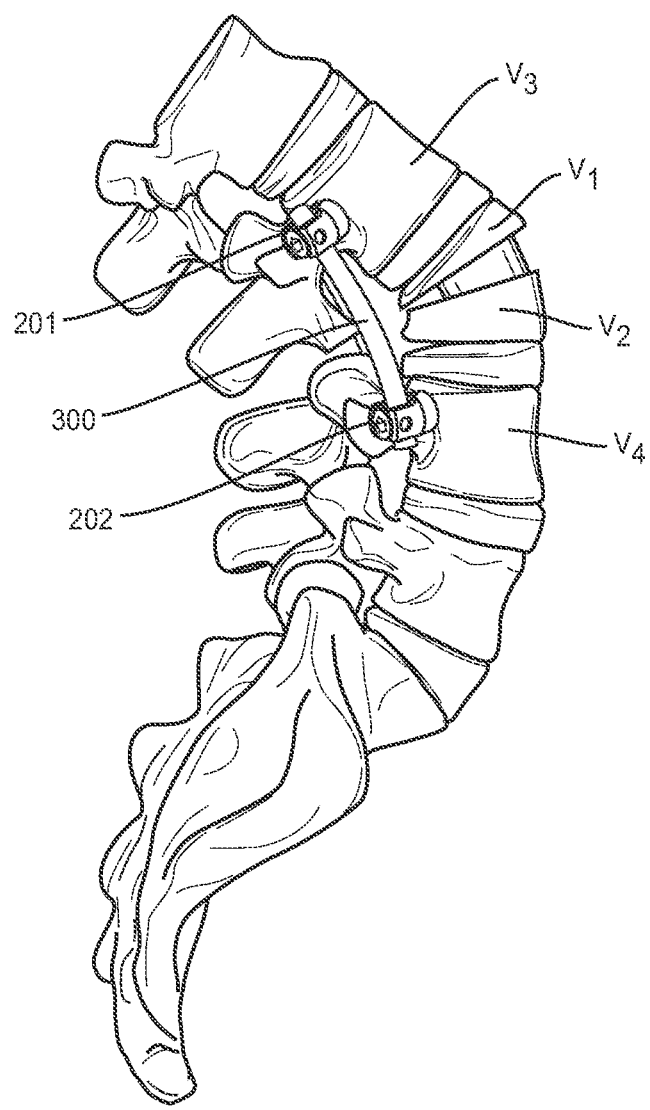
FIG. 3 is a perspective view of a spine with an intrabody implant, according to one embodiment.

Referring to FIGS. 1-3, a method for surgically adjusting a curvature of the spine is provided. In one embodiment, a vertebral body V is selected for an osteotomy procedure which may include removing portions of the pedicle P, spinous processes SP and/or facet joint structures F at the level of the vertebral body V. While level L3 is depicted in FIG. 1, a surgeon may apply the procedure described herein to any number of spinal levels in the lumbar, thoracic, or cervical spine to introduce a corrective curvature to the spine. In general, the disc and vertebra above and below the disc comprise one segment of the spine—usually called a spinal level or spinal segment.

As shown in FIG. 2, the method may further comprise removing a wedge-shaped portion of a single vertebral body V (see FIG. 1) to form two at least partially separated portions V1, V2 of the single vertebral body V. A surgeon may select and/or measure a corrective angle θ to serve as the basis for this step. However, and as described further herein, the acute angle α defined by the surfaces 110, 120 of the implant 100 (see FIG. 5) may be used to ensure that the completed spinal surgery results in a desired level of spinal curvature (see FIG. 3) regardless of the angle θ of the removal cut made by the surgeon as part of the removal step. As described herein with respect to FIG. 1, the removing step may comprise a pedicle subtraction osteotomy (PSO) procedure wherein the pedicle P, spinous process SP, and/or portions of the facet joint structure F are completely or partially removed from the vertebral body.

The method may further comprise providing a wedge-shaped intrabody implant 100 (as described further herein with respect to FIGS. 4-6) comprising a first surface 110 and a second surface 120, wherein the second surface 120 may be disposed at an acute angle α to the first surface 110. In some embodiments as shown in FIG. 4, the intrabody implant 100 may be provided with an aperture 101 extending through the wedge-shaped intrabody implant 100 to allow for bone growth therethrough. In other embodiments, the method may further comprise packing the aperture 101 with a bone-growth promotion material prior to the placing step described herein with respect to FIG. 3.

As shown in FIG. 3, the method further comprises placing the wedge-shaped intrabody implant 100 between the two at least partially separated portions V1, V2 of the single vertebral body V, and closing or bringing into closer proximity the two at least partially separated portions V1, V2 of the single vertebral body about the intrabody implant 100. Therefore, the two at least partially separated portions V1, V2 of the single vertebral body are oriented at a correction angle relative to one another. Preferably, the resulting correction angle may be substantially predictable based on the selected implant. For example, in some embodiments, the correction angle may be within a selected number of degrees of the acute angle defined by the intrabody implant. In some embodiments, the range of difference between the correction angle and the acute angle may be relatively wide (i.e. 10-90 degrees). In other embodiments, the range of difference between the correction angle and the acute angle may be relatively narrow (i.e. 0-10 degrees).

According to various method embodiments, the correction angle of the spinal column defined at least in part by the acute angle α of the intrabody implant may provide a lordotic correction to a spinal column at the level of the single vertebral body V. In other embodiments, the implant direction may be reversed such that the correction angle of the spinal column defined at least in part by the acute angle α of the intrabody implant may provide a kyphotic correction to a spinal column at the level of the single vertebral body V. In some embodiments, the various embodiments of the present invention may provide a correction angle across multiple levels (such that the acute angles α of several intrabody implants 100 may provide a lordotic correction to a spinal column across two or more levels). In such embodiments, the removing, providing, placing and closing or bringing into closer proximity steps disclosed herein may be repeated across two or more levels of the human spine to achieve an overall spinal correction across the two or more levels.

Figure 7:
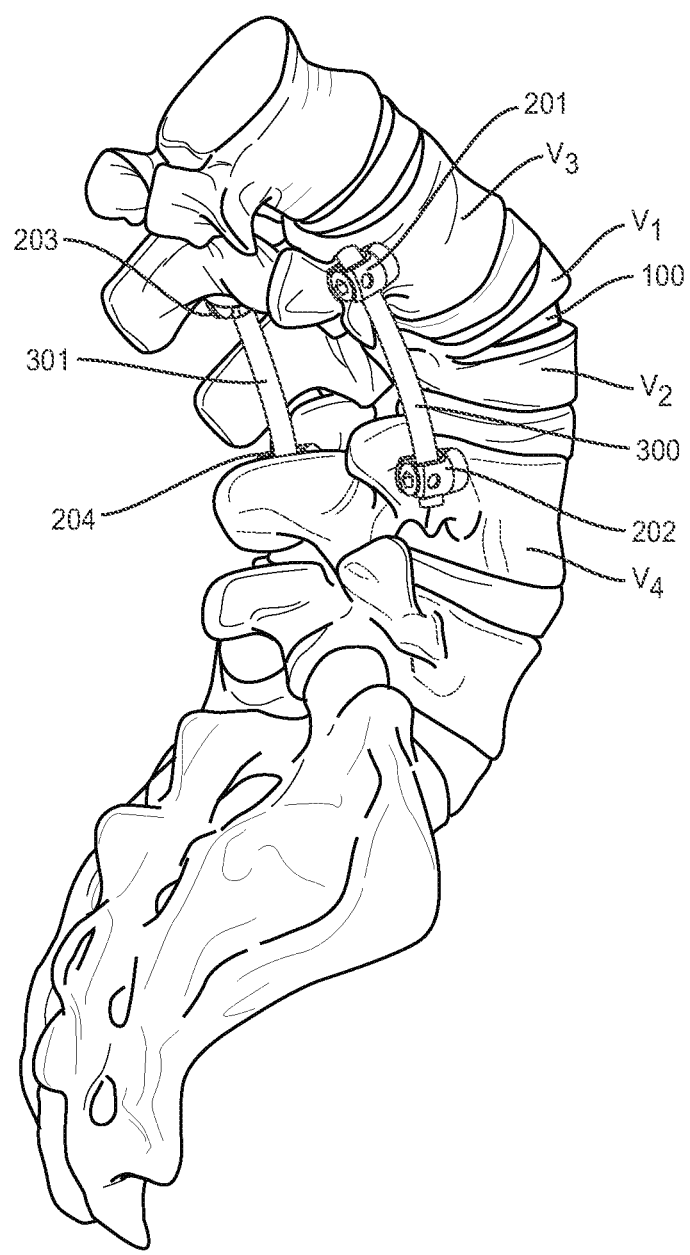
FIG. 7 is a perspective view of a spine with an intrabody implant system, according to one embodiment.

In some method embodiments, the closing or bringing into closer proximity step described herein may further comprise securing the two at least partially separated portions V1, V2 of the vertebral body V about the implant 100 using an extradiscal stabilization system (which may include, for example, a rod 300 and pedicle screw 201, 202 construct as shown generally in FIGS. 3 and 7. The pedicle screws 201, 202 may be inserted into the pedicles of adjacent vertebral bodies V3, V4 and connected via rod 300 that may be shaped and/or bent by the surgeon to further reinforce the corrective angle sought as part of the surgical procedure. FIG. 7 shows a perspective view of a bi-lateral screw 201, 202, 203, 204 and rod 300, 301 construct that may also be used to reinforce the corrected spinal curvature using the various methods described here. Various screw and rod systems may be used for the reinforcement step, including but not limited to the SOLERA® and LEGACY® extradiscal stabilization systems offered by Medtronic® Spine.

Figure 8:
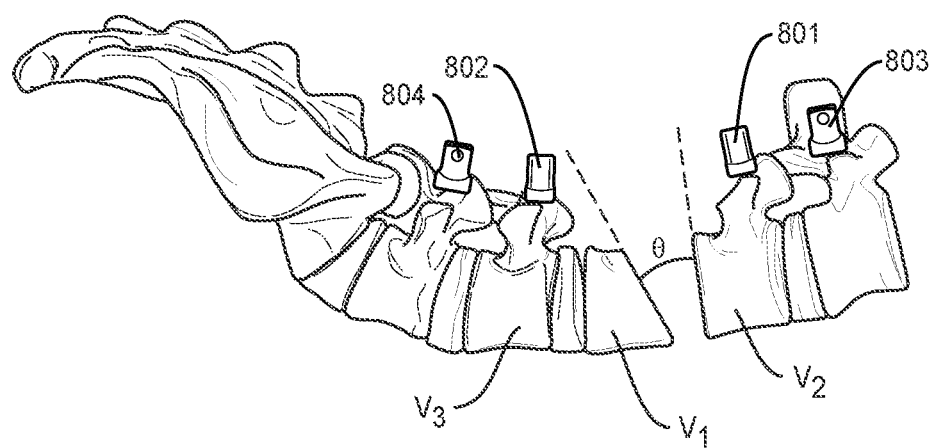
FIG. 8 is a side view of a spine after the initial removal of bony material from an osteotomy procedure and placement of pedicle screws.

Referring now to FIGS. 8-16, a method for surgically adjusting a curvature of the spine is provided. In one embodiment, a vertebral body is selected for an osteotomy procedure and a portion of the vertebral body is removed to form two at least partially separated portions of the single vertebral body as discussed above. The removed portion may be wedge-shaped or any other suitable shape. Alternatively, as shown in FIG. 8, a wedge shaped portion of the single vertebral body V1 may be removed together with an adjacent intervertebral disc, or a portion thereof, to form a gap in the spine. In such instances, vertebral body or body portion V1 may contact adjacent vertebral body or body portion V2 directly in a "bone-on-bone" closure, or a wedge-shaped or other-shaped intrabody implant may be disposed therebetween as discussed above. A surgeon may select and/or measure a corrective angle θ to serve as the basis for this step. As described above with respect to FIGS. 1 and 2, the removing step may comprise a pedicle subtraction osteotomy (PSO) procedure wherein the pedicle P, spinous process SP, and/or portions of the facet joint structure F are completely or partially removed from the vertebral body.

Figure 9:
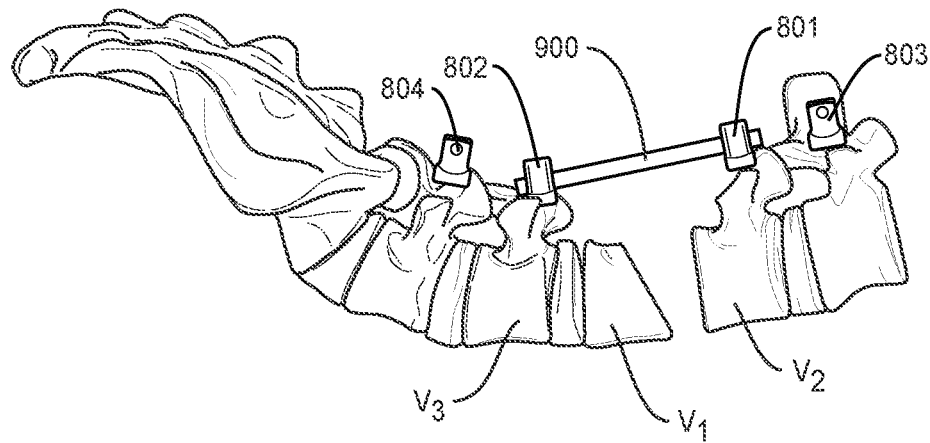
FIG. 9 is a side view of a spine with a rod placed in pedicle screws prior to closure of portions of the spine, according to one embodiment.
Figure 10:
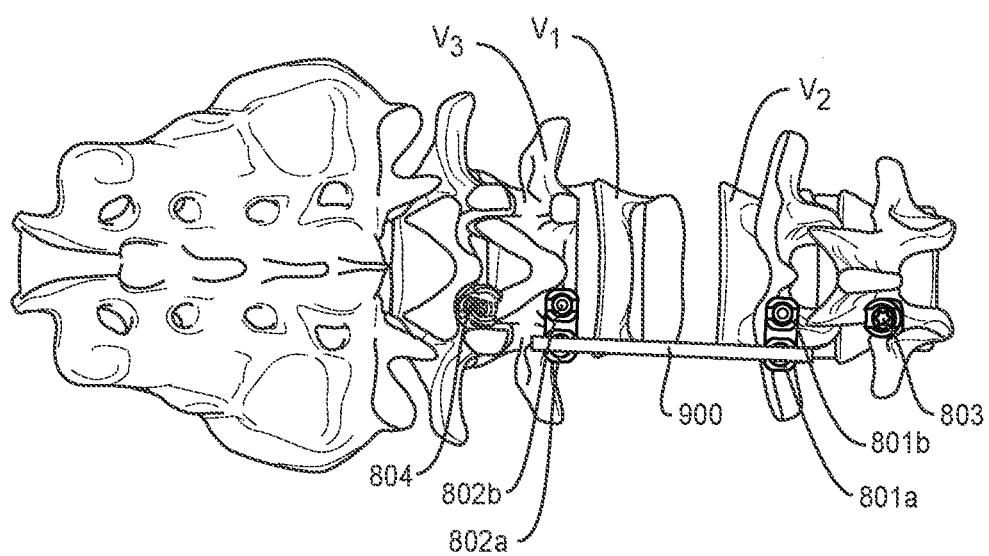
FIG. 10 is a top view of a spine with a rod placed prior to closure of portions of the spine, according to one embodiment.
Figure 11:
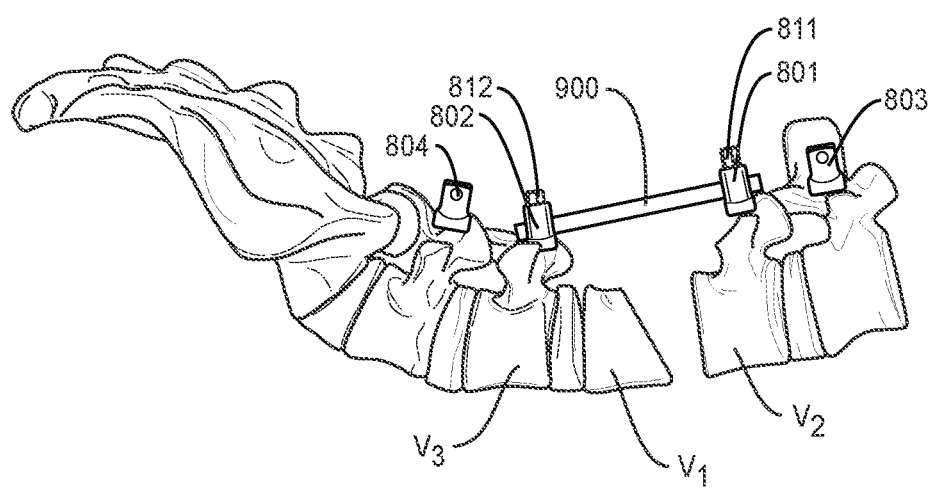
FIG. 11 is a side view of a spine with a rod placed and secured prior to closure of portions of the spine, according to one embodiment.
Figure 12:
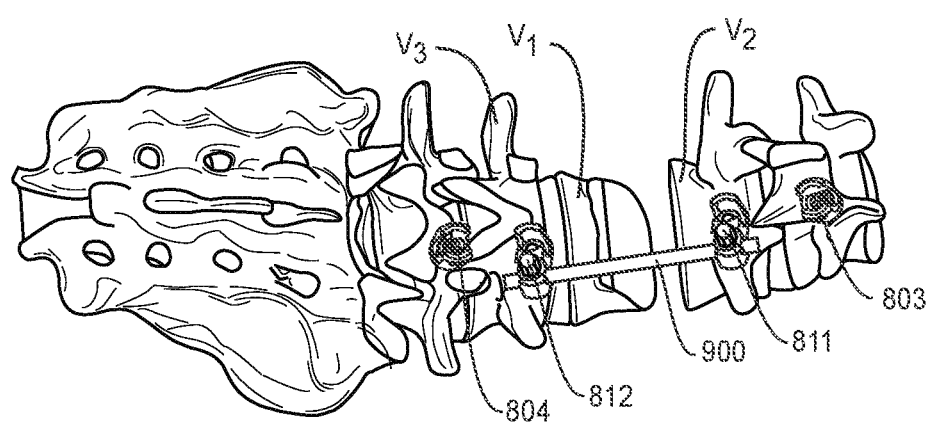
FIG. 12 is a top view of a spine with a rod placed and secured prior to closure of portions of the spine, according to one embodiment.

The method may further comprise the step of inserting pedicle screws 801 and 802 into vertebrae V2 and V3 adjacent to the vertebral body selected for the osteotomy procedure, or superior and inferior to the gap in the spine formed by removal of a vertebral body, intervertebral disc, or portions, or a combination thereof. As shown in FIGS. 9 and 10, a rod 900 is placed in heads of pedicle screws 801 and 802. The rod 900 may be secured with set screws 811 and 812, as shown in FIGS. 11 and 12, or other closure mechanisms (for example, wires or plates). In one embodiment of the invention, pedicle screws 801 and 802 may be dual headed screws, such as, for example, those disclosed in co-pending application Ser. No. 15/483,824, incorporated herein in its entirety, and rod 900 may be secured in a first head 801a and 802a of pedicle screws 801 and 802. Second head 801b and 802b of pedicle screws 801 and 802 remain available for securing, e.g., a stabilization rod, as discussed below. Alternatively, offset connectors may be applied or inserted into one or more screw heads to effectively create multi-headed screws in place of or in addition to the use of one or more dual-headed screws. Rod 900 may help restrict any shift in bony structures V1 and V2 as portions of the spine come closer together and the adjacent faces of V1 and V2 are brought towards one another to the corrected spinal curvature. In some embodiments, a second set of pedicle screws and rod are placed bilaterally to pedicle screws 801 and 802 and rod 900 to provide additional alignment control.

The method further comprises the step of closing or bringing into closer proximity the at least partially separated portions of the single vertebral body such that the first and second pedicle screw advance towards one another along the rod. In this manner, the alignment of the spine is ensured and subluxation of the vertebrae is reduced or prevented. Set screws 811 and 812 or other closure mechanisms securing rod 900 into pedicle screws 801 and 802 may be selectively tightened and loosened during this step to control the advancement towards, or distance between, the pedicle screws as the bony structures V1 and V2 are brought towards one another. Bony structures V1 and V2 may be brought towards one another using any standard means or devices as known by one of ordinary skill in the art. For example, a pedicle subtraction osteotomy may be performed on a hinged operating table with the ends of the table slightly below the hinge at the start of the procedure. During closure of the spine, the hinged table may be flattened, thereby bringing bony structures V1 and V2 towards one another.

A surgeon may also use any other means, tool, or apparatus to adjust the distance between the bony structures V1 and V2 and/or pedicle screws 801 and 802, including, but not limited to, distractors, compressors, extenders, or controllers. For example, it may be necessary to adjust the distance between bony structures V1 and V2 independently from pedicle screws 801 and 802 in order to adjust the angle of the adjacent faces of V1 and V2. By using a combination of tightening and loosening set screws 811 and 812, or other closure mechanisms securing rod 900 in pedicle screws 801 and 802, such as distractors, compressors, extenders, controllers, and/or other tools as may be known to those of ordinary skill in the art, a surgeon may adjust the distance between pedicle screws 801 and 802 along rod 900, either increasing, decreasing, or maintaining the distance, while moving adjacent faces V1 and V2. Distractors known in the art may be used, e.g., to hold pedicle screws 801 and 802 apart as portions of the spine are manipulated, Compressors known in the art may further be used, e.g., to bring pedicle screws 801 and 802 closer together as portions of the spine are manipulated. Exemplary tools, e.g., compressors and distractors, are disclosed in, e.g., U.S. Pat. No. 7,686,814, incorporated herein by reference in its entirety. Extenders may be attached to, e.g., pedicle screws 801 or 802 and may alter the distance and/or relative orientation therebetween in order to ease connection to rod 900 or other spinal rods, or to provide additional means for interaction. Exemplary extenders are disclosed in, e.g., U.S. Pat. Nos. 8,663,289, 8,727,972, and 8,828,059, all incorporated herein by reference in their entirety. A controller that may be, e.g., secured to pedicle screws 801 and 802 and may be used to selectively apply compression or distraction forces thereto is disclosed in, e.g., U.S. Pat. No. 9,402,660, incorporated herein by reference in its entirety.

Figure 13:
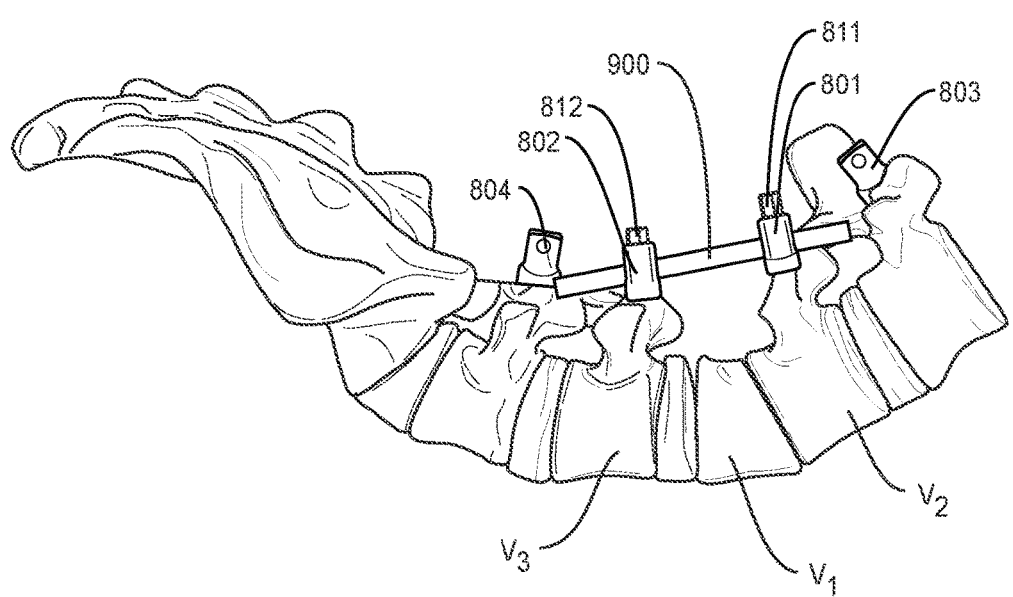
FIG. 13 is a side view of a spine with a rod placed and secured after closure of portions of the spine, according to one embodiment.
Figure 14:
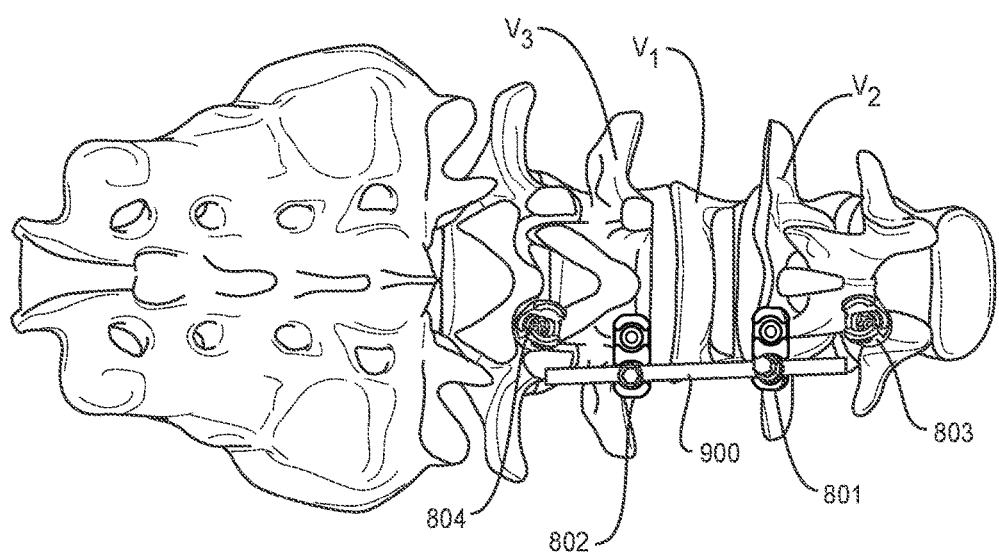
FIG. 14 is a top view of a spine with a rod placed and secured after closure of portions of the spine, according to one embodiment.

Referring now to FIGS. 13 and 14, the spine has been closed and adjacent faces of bony structures V1 and V2 have been brought into "bone-on-bone" contact. In comparison with FIGS. 9-12, the distance between pedicle screws 801 and 802 is decreased due to advancement towards one another along rod 900. In this manner, the alignment of the spine is improved and subluxation of the vertebrae reduced or prevented during closure of, or bringing into closer proximity, portions of the spine.

Figure 15:
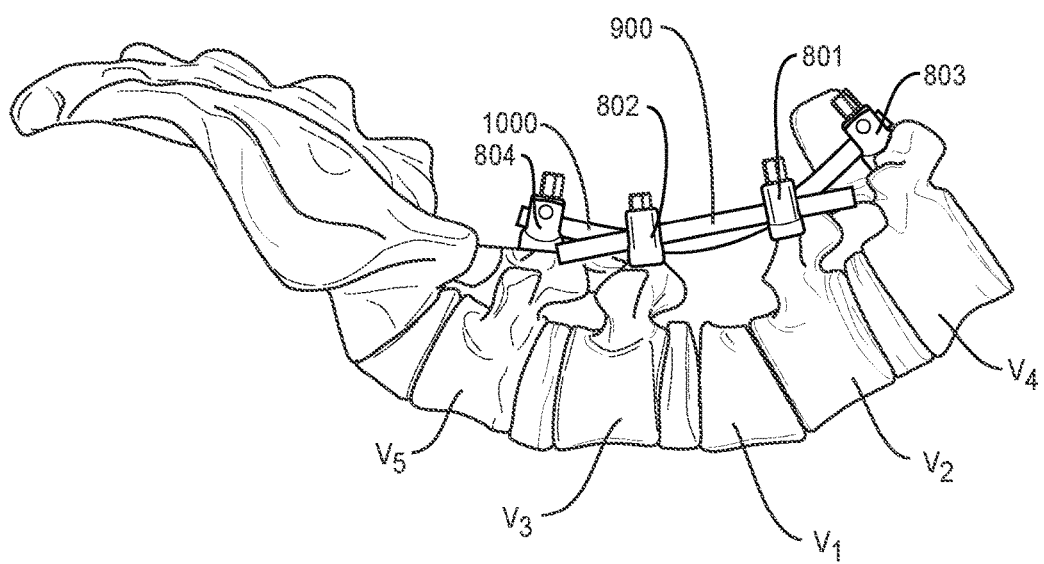
FIG. 15 is a side view of a spine after closure of portions of the spine with a stabilization rod secured, according to one embodiment.
Figure 16:
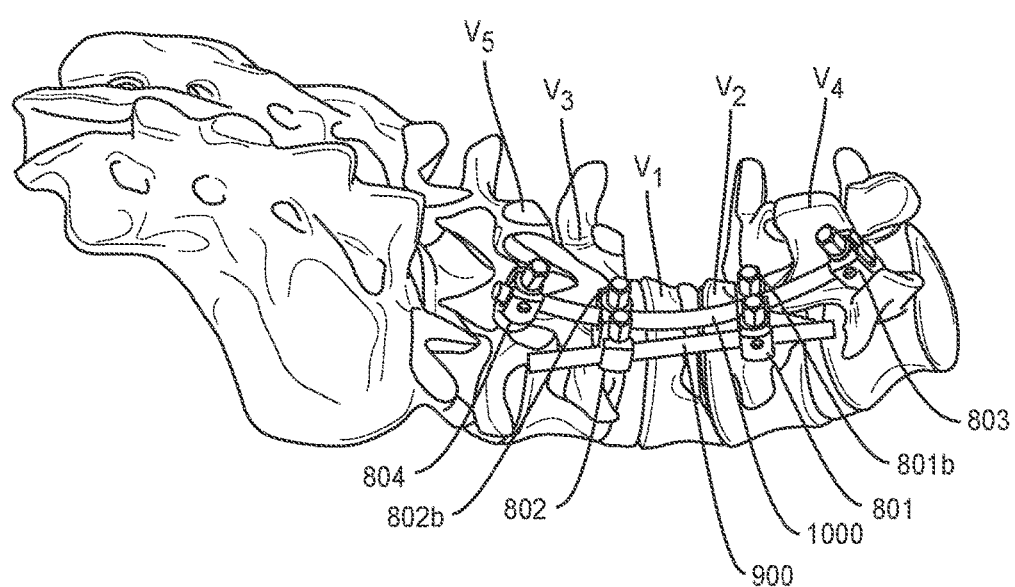
FIG. 16 is a perspective view of a spine after closure of portions of the spine with a stabilization rod secured, according to one embodiment.

In some method embodiments, the closing or bringing into closer proximity step described herein may further comprise securing a corrected spinal curvature using an extradiscal stabilization system (which may include, for example, a stabilization rod 1000 and pedicle screws 801, 802, 803, and 804 as shown generally in FIGS. 15 and 16). Pedicle screws 803 and 804 may be inserted into the pedicles of adjacent vertebral bodies V4, V5 and connected via stabilization rod 1000. Rod 1000 may be shaped and/or bent as desired to further reinforce the corrective angle sought as part of the surgical procedure. FIG. 15 shows a side view of a construct comprising pedicle screws 801, 802, 803, 804, rod 900, and stabilization rod 1000, which may also be used to reinforce the corrected or adjusted spinal curvature using the various methods described here, while FIG. 16 shows a perspective view of the construct with stabilization rod inserted into second heads 801b and 802b of pedicle screws 801 and 802. Various screw and rod systems may be used for the reinforcement step, including but not limited to the SOLERA® and LEGACY® extradiscal stabilization systems offered by Medtronic® Spine.

Referring now to FIGS. 3-6, an intrabody implant 100 is disclosed for placement between at least two separated portions V1, V2 of a bony structure such as a vertebral body V. The implant 100 may be formed in whole or in part from a variety of biocompatible materials suitable for long-term implantation. For example, the implant 100 may be preferably formed of a polymer such as PEEK.

The components of implant 100 can be fabricated from a variety of biologically acceptable materials suitable for medical applications, including metals, synthetic polymers, ceramics and bone material and/or their composites, depending on the particular application and/or preference of a medical practitioner. For example, the components of implant 100, individually or collectively, can be fabricated from materials such as stainless steel alloys, commercially pure titanium, titanium alloys, Grade 5 titanium, superelastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephtalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, tricalcium phosphate, or fluorapatite, tri-calcium phosphate (TCP), HA-TCP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

According to the various embodiments provided herein, the implant 100 may comprise a first surface 110 configured for engaging a first V1 of the at least two separated portions of the bony structure. The implant 100 further comprises a second surface 120, disposed opposite the first surface 110, and configured for engaging a second V2 of the at least two separated portions of the bony structure. As shown in FIG. 5, the first and second surfaces 110, 120 may be disposed at an acute angle α relative to one another. The angle α may range widely from zero to 90 degrees. However, in some preferable embodiments the angle α may range from 10 to 30 degrees. In other more preferable embodiments, the angle α may range from 15 to 25 degrees.

As shown in FIGS. 4 and 5, the implant 100 may further comprise a wall 150 disposed between the first and second surfaces 110, 120. The wall 150 comprises an anterior portion 130 and a posterior portion 140. As shown in FIG. 5, the posterior portion 140 has a posterior height and the anterior portion 130 has an anterior height, wherein the posterior and anterior heights are unequal to form the preferably acute angle α between the first surface 110 and the second surface 120 of the implant 100. In some embodiments, as shown in FIG. 5, the posterior height may be less than the anterior height such that the angle α of the implant 100 introduces a lordotic angle between the first and second portions V1, V2 of the bony structure V (see FIG. 3, for example). Furthermore, as shown in FIG. 5, the posterior portion 140 and/or anterior portion 130 of the implant may be provided with a convex profile between the first and second surfaces 110, 120 to aid in the ease of insertion of the implant 100. The profile may also, in alternate embodiments, be chamfered and/or provided with edge radii to allow for easier insertion of the implant 100 from either the posterior or anterior directions.

FIG. 6 shows a top view of an implant 100 according to one embodiment wherein the first and second surfaces 110, 120 define an aperture 101 extending through the implant 100 to allow for bone growth through the implant 100 from the first portion V1 of the bony structure V to the second portion V2 (see FIG. 3, for example). The aperture 101 may also be packed with bone growth promoting material, including but not limited to bone allograft, bone xenograft, bone autograft, bone morphogenetic protein (BMP) and/or combinations thereof. Furthermore, as shown in FIG. 6, the implant 100 may be formed in a shape that conforms to the anatomy of the human spine. For example, the posterior portion 140 of the wall 150 may comprise an outer concave surface configured to conform to a posterior anatomy of the bony structure V. Furthermore, the anterior portion 130 of the wall 150 may comprise an outer convex surface configured to conform to an anterior anatomy of the bony structure V.

Referring again to FIG. 6, the implant 100 may include a width W extending substantially parallel to the anterior portion 130 and the posterior portion 140. The width W of the implant 100 may be chosen to substantially fill the width of the vertebral body V or other bony structure where the intrabody is intended to be placed after osteotomy. For example, in some embodiments, the width W may be at least 40 mm. In other embodiments, the width W may be at least 50 mm (when used, for example, in the lower lumbar region). In other embodiments, the width W may be tailored for use in smaller vertebral bodies (for example, in smaller patients or in the upper thoracic or cervical spine). In some such embodiments, the width W may be in the range of 15-40 mm (or 25-30 mm in some preferable cervical and thoracic embodiments). The depth of the implant 100 may also vary accordingly (wherein the depth is measured perpendicular to the width W from the anterior portion 130 to the posterior portion 140). In some embodiments, the depth may range from 10 mm to 50 mm (and preferably from 15-20 mm in certain embodiments).

As shown in FIGS. 4 and 6, the first surface 110 and second surface 120 of the implant 100 may further comprise a plurality of surface features 112 extending outward from the surfaces 110, 120 to engage a complementary surface of the bony structure V. For example, the surface features 112 may include, but are not limited to: ridges, teeth, pyramidal structures, roughened irregular projections and/or combinations thereof. The surface features 112 may be optimized in shape and/or directional orientation to resist the expulsion of the implant 100 from between the portions V1, V2 of the bony structure when the patient applies weight forces to the spine during the course of standing or movement. For example, the surface features 112, may comprise rows of teeth (see FIG. 5) having a substantially right-triangular profile wherein the teeth are sloped upwards towards the anterior portion 130 of the wall 150 of the implant 100. In other embodiments, the implant 100 may further comprise a coating applied to one or more of the surfaces 110, 120 and/or the wall 150 to encourage bone growth onto the implant 100. Such coatings may include, but are not limited to: gold, titanium, hydroxyapatite (HA) and/or combinations thereof. The coatings may be applied with a roughened texture so as to provide a plurality of irregular projections that may serve as surface features 112 to also resist expulsion of the implant 100 after implantation. In other embodiments, the implant 100 may have substantially smooth surfaces 110, 120 and wall 150 having no projections or surface features.

In other embodiments, the implant 100 may, for example, be expandable in a number of ways, including by, e.g., sliding wedge, turnbuckle, ratchet, hinge, expandable balloon, ratchets, stackable implants, vaneers slid inside the implant top and bottom like shims, via the use of springs, or via telescoping designs. Exemplary expandable implants and methods of their use are disclosed in, e.g., U.S. patent application Ser. Nos. 14/885,472, 15/008,805, and, 15/009,582, and U.S. Pat. Nos. 7,118,579, 7,655,027, 7,922,729, and 8,771,321, all incorporated herein by reference in their entirety. Once expanded, graft and/or other bone growth promoting material inserted into the implant by various cannula, tubing, syringes, tamps, or other mechanisms as known to those of ordinary skill in the art. An exemplary graft and/or bone growth material delivery device is disclosed in, e.g., U.S. Pat. No. 8,092,464, incorpored herein by reference in its entirety.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A method for surgically adjusting a curvature of a spine comprising vertebrae, the method comprising:
   removing a portion of a single vertebral body of the spine to form two at least partially separated portions of the single vertebral body;
   providing a wedge-shaped intrabody implant comprising a first surface and a second surface, the second surface disposed at an acute angle to the first surface, and wherein the first and second surfaces define an aperture extending through the implant;
   placing the wedge-shaped intrabody implant between the two at least partially separated portions of the single vertebral body;
   inserting a first pedicle screw into a second vertebral body superior to the single vertebral body and a second pedicle screw into a third vertebral body inferior to the single vertebral body;
   inserting a third pedicle screw in a vertebrae superior to the first pedicle screw and a fourth pedicle screw in a vertebrae inferior to the second pedicle screw;
   connecting the first pedicle screw and the second pedicle screw with a first rod;
   connecting the first, second, third, and fourth pedicle screws with a second rod;
   bringing into closer proximity the two at least partially separated portions of the single vertebral body such that the first and second pedicle screw advance towards one another along the first rod.

2. The method as recited in claim 1, wherein after the step of bringing into closer proximity the at least partially separated portions of the single vertebral body are oriented at a correction angle relative to one another.

3. The method as recited in claim 2, wherein the correction angle provides a lordotic correction to a spinal column at the level of the single vertebral body.

4. The method as recited in claim 2, wherein the correction angle provides a kyphotic correction to a spinal column at the level of the single vertebral body.

5. The method as recited in claim 1, wherein the removing step comprises a pedicle subtraction osteotomy (PSO) procedure.

6. The method as recited in claim 1, wherein the step of bringing into closer proximity further comprises securing the two at least partially separated portions of the single vertebral body relative to one another using an extradiscal stabilization system.

7. The method as recited in claim 1, further comprising repeating the removing, inserting, connecting, and step of bringing into closer proximity across one, two or more levels of the human spine to achieve an overall spinal correction across the one, two or more levels.

8. The method as recited in claim 1, further comprising, packing the aperture with a bone-growth promotion material prior to the placing step.

9. The method as recited in claim 1, wherein the acute angle is between 10 degrees and 30 degrees.

10. The method as recited in claim 9, wherein the acute angle is between 15 degrees and 25 degrees.

11. The method as recited in claim 1, wherein the first pedicle screw is positioned on a lateral side of spinous processes of the second vertebral body, and wherein the second pedicle screw is positioned on the same lateral side of spinous processes of the third vertebral body.

12. The method as recited in claim 1, wherein the first and second pedicle screws are dual headed screws and the first rod connects a first head of the first pedicle screw with a first head of the second pedicle screw.

13. The method as recited in claim 12, wherein the second rod connects a second head of the first pedicle screw with a second head of the second pedicle screw.

14. A method for surgically adjusting a curvature of a spine comprising vertebrae, the method comprising:
   removing a portion of a single vertebral body of the spine to form two at least partially separated portions of the single vertebral body;
   providing a wedge-shaped intrabody implant comprising a first surface and a second surface, the second surface disposed at an acute angle to the first surface, and wherein the first and second surfaces define an aperture extending through the implant;
   placing the wedge-shaped intrabody implant between the two at least partially separated portions of the single vertebral body;
   inserting a first pedicle screw into a second vertebral body superior to the single vertebral body and a second pedicle screw into a third vertebral body inferior to the single vertebral body;
   connecting the first pedicle screw and the second pedicle screw with a rod; and
   bringing into closer proximity the two at least partially separated portions of the single vertebral body such that the first and second pedicle screw advance towards one another along the rod.

15. The method as recited in claim 14, wherein after the step of bringing into closer proximity the at least partially separated portions of the single vertebral body are oriented at a correction angle relative to one another.

16. The method as recited in claim 14, further comprising, packing the aperture with a bone-growth promotion material prior to the placing step.

17. The method as recited in claim 14, wherein the acute angle is between 10 degrees and 30 degrees.

18. The method as recited in claim 17, wherein the acute angle is between 15 degrees and 25 degrees.

\* \* \* \* \*